US007354403B2

(12) United States Patent
Mochizuki

(10) Patent No.: US 7,354,403 B2
(45) Date of Patent: Apr. 8, 2008

(54) CUFF APPARATUS AND SPHYGMOMANOMETER COMPRISING THE SAME

(75) Inventor: Hiroshi Mochizuki, Fuji (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 270 days.

(21) Appl. No.: 10/764,507

(22) Filed: Jan. 27, 2004

(65) Prior Publication Data

US 2004/0186385 A1    Sep. 23, 2004

Related U.S. Application Data

(63) Continuation of application No. PCT/JP02/07617, filed on Jul. 26, 2002.

(30) Foreign Application Priority Data

Jul. 27, 2001    (JP) .............................. 2001-227045

(51) Int. Cl.
*A61B 5/02* (2006.01)
(52) U.S. Cl. ........................ 600/499; 600/490; 600/493
(58) Field of Classification Search ........ 600/490–503, 600/300, 301, 481, 483–485; 606/201–203
See application file for complete search history.

(56) References Cited

U.S. PATENT DOCUMENTS

| | | | |
|---|---|---|---|
| 2,444,161 A | | 6/1948 | Hanafin |
| 3,258,009 A | | 6/1966 | London |
| 3,752,147 A | * | 8/1973 | Castro et al. ............... 600/499 |
| 4,308,871 A | | 1/1982 | Shouda et al. |
| 4,667,672 A | | 5/1987 | Romanowski |
| 5,031,630 A | * | 7/1991 | Hirano et al. ............... 600/493 |
| 5,277,187 A | * | 1/1994 | Pillsbury ..................... 600/495 |
| 5,406,954 A | * | 4/1995 | Tomita ........................ 600/493 |
| 5,511,551 A | * | 4/1996 | Sano et al. .................. 600/499 |
| 5,649,535 A | * | 7/1997 | Voith ........................... 600/493 |
| 5,651,369 A | * | 7/1997 | Tomita ........................ 600/493 |
| 5,680,868 A | * | 10/1997 | Kahn et al. .................. 600/494 |
| 5,840,036 A | * | 11/1998 | Voith ........................... 600/493 |
| 5,873,836 A | * | 2/1999 | Kahn et al. .................. 600/493 |
| 6,705,998 B2 | * | 3/2004 | Stergiopoulos et al. ..... 600/493 |

(Continued)

FOREIGN PATENT DOCUMENTS

DE    28 00 982    7/1978

(Continued)

OTHER PUBLICATIONS

Abstract of JP 2004195056 A.*

(Continued)

*Primary Examiner*—Charles A. Marmor, II
*Assistant Examiner*—Navin Natnithithadha
(74) *Attorney, Agent, or Firm*—Buchanan Ingersoll & Rooney PC

(57) ABSTRACT

A plurality of cushions are provided in the airbag of a cuff apparatus, spaced apart from one another and thus maintaining the airbag in an inflated state before compressed air is introduced into the airbag. This shortens the time required to supply the compressed air and minimizes the resistance to the body part being inserted into the cuff apparatus. Therefore, the body part can smoothly enter the cuff apparatus and the flow of blood can be sufficiently suppressed.

28 Claims, 10 Drawing Sheets

U.S. PATENT DOCUMENTS

2006/0058689 A1* 3/2006 Kishimoto et al. ......... 600/499

FOREIGN PATENT DOCUMENTS

| DE | 28 37 707 A1 | 3/1980 |
| DE | 35 33 513 A1 | 4/1987 |
| EP | 0 615 722 A1 | 9/1994 |
| JP | 4-48163 | 11/1992 |
| JP | 4-50005 | 11/1992 |
| JP | 2527453 | 11/1996 |
| JP | 2004195056 A * | 7/2004 |
| WO | 80/00005 | 1/1980 |

OTHER PUBLICATIONS

European Search Report dated Jul. 13, 2007.

* cited by examiner

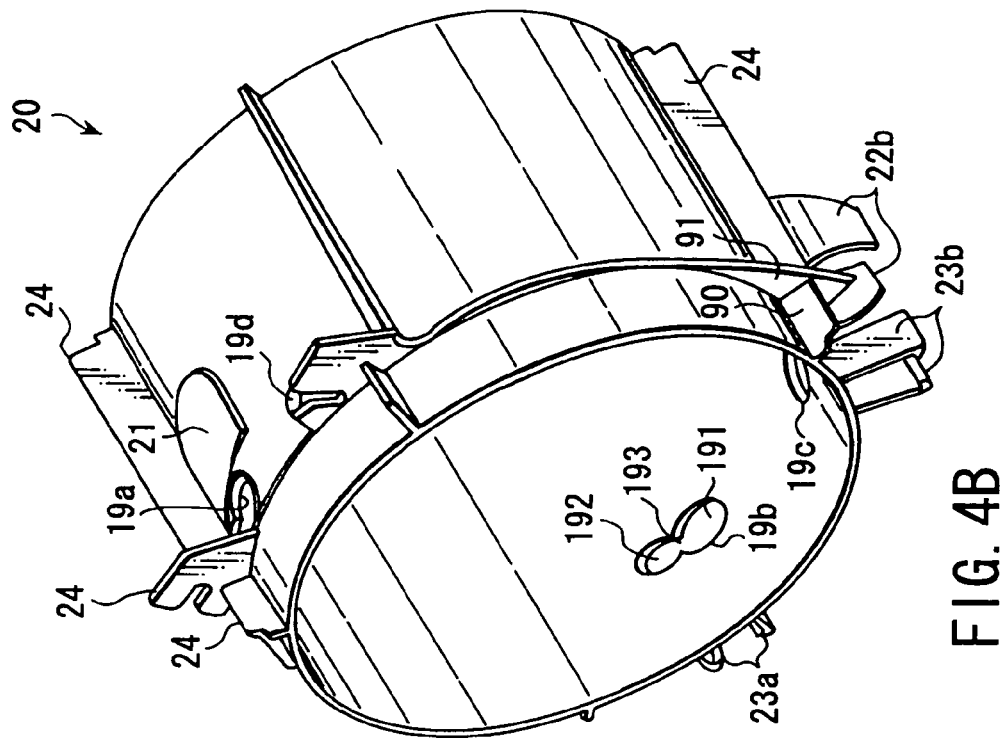
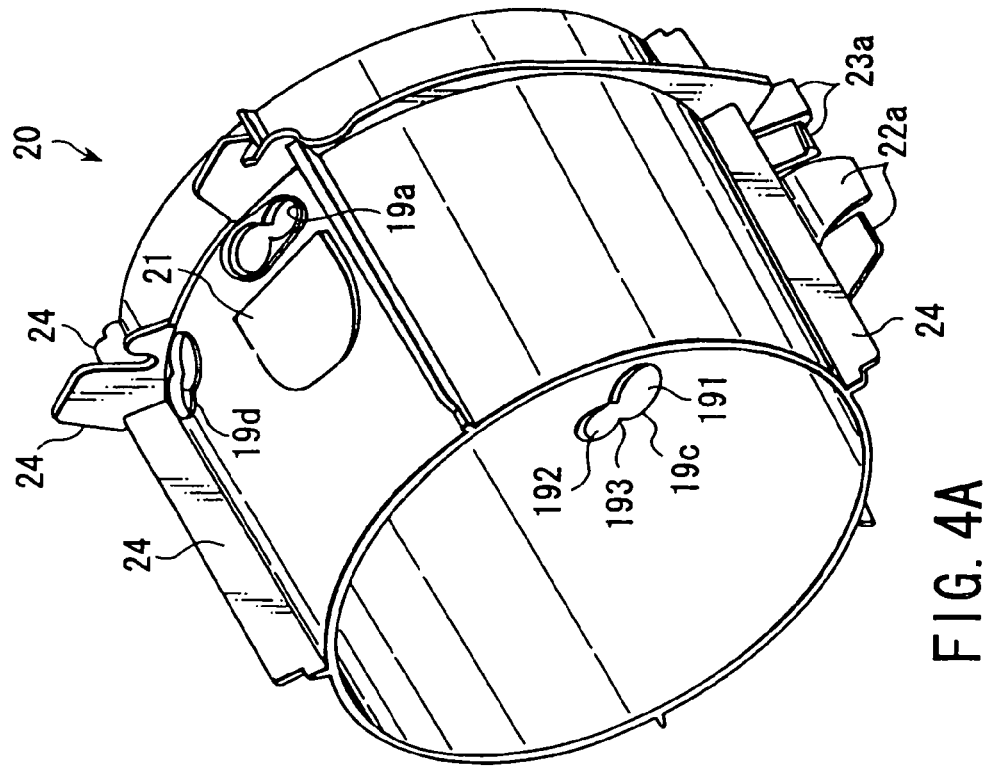

CUFF APPARATUS AND SPHYGMOMANOMETER COMPRISING THE SAME

CROSS-REFERENCE TO RELATED APPLICATIONS

This is a Continuation Application of PCT Application No. PCT/JP02/07617, filed Jul. 26, 2002, which was not published under PCT Article 21(2) in English.

This application is based upon and claims the benefit of priority from the prior Japanese Patent Application No. 2001-227045, filed Jul. 27, 2001, the entire contents of which are incorporated herein by reference.

BACKGROUND OF THE INVENTION

1. Field of the Invention

The present invention relates to a cuff apparatus for measuring the blood pressure, which has a cylindrical section containing an air bag (a bladder) and which is designed to suppress the flow of blood in a body part inserted in the cylindrical section. The invention relates also to a sphygmomanometer that comprises such a cuff apparatus.

2. Description of the Related Art

Cuff apparatuses for measuring blood pressures are known. They comprise a cylindrical section which incorporates an airbag (a bladder) and into which a body part (upper arm or forearm) is inserted so that the flow of blood in the body part may be suppressed. (Hereinafter, they shall be called "cuff apparatuses of body-part insertion type.") As FIG. 12 shows (Unexamined Published Japanese Patent No. 10-314123), a cuff apparatus may comprise a cuff 100, an electric motor 200, and tapes 300. The motor 200 and the tapes 300 are used to pull and taken up the cuff 100.

The cuff apparatus, wherein the cuff is pulled and taken up, consumes much electric power, has a complex structure, is difficult to assemble, and is large and heavy.

The cuff may be shaped like a hollow cylinder and may incorporate an airbag (a bladder) that has a diameter much greater than the diameter of the body part (upper arm or forearm). Compressed air may be introduced into the airbag, reducing the inside diameter of the cuff until the cuff fits on the body part.

The cuff apparatus, in which the cuff fits on the body part as compressed air is introduced, is indeed smaller and lighter than the type in which the cuff is taken up. However, it is disadvantageous in the following respects.

First, the airbag needs to have a volume about four to five times as large as in the cuff of ordinary type, which is manually wrapped around the body part. It takes more time to introduce compressed air into the airbag. In view of this, four to five air-compressing pumps may be used. Alternatively, an air-compressing pump with an output capacity of four to five times as much may be employed. In either case, much power is consumed, and the cuff apparatus must comprise an AC power supply. Consequently, the sphygmomanometer becomes larger and heavier.

Second, the cylindrical airbag has a large inside diameter even before compressed air is supplied into it. The inside diameter of the cylindrical bag greatly changes (decreases) as air is forced into the airbag. Thus, the inner circumferential surface of the airbag (i.e., the surface contacting the body part) may have wrinkles by the time the bag fits on the body part, particularly at the part, which lies near the arteries existing in the body part. Wrinkles, if formed, may decrease the ability of suppressing the flow of blood. In a cuff apparatus for use in combination with a sphygmomanometer with which the sound of the bloodstream (i.e., Korotkoff sound) is detected to measure the blood pressure, the cuff needs to have a microphone for detecting the Korotkoff sound. The microphone may not contact the body part due to the wrinkles formed on the inner circumferential surface of the airbag. Consequently, the Korotkoff sound may not be detected correctly.

Third, the airbag, i.e., a cylindrical member secured to the inner circumferential surface of the hollow cylindrical chassis (case) into which the body part should be inserted, cannot sufficiently suppress the flow of blood at its ends. Hence, the airbag fails to suppress the flow of blood as is desired, if the chassis holds the body part, with the arteries located at the ends of the airbag.

Fourth, the cuff apparatus is difficult to assemble, because the airbag must be secured to the chassis with double-side adhesive tape or the like, while holding nozzles (conduits) at prescribed positions. Note that the nozzles are indispensable components for introducing and discharging compressed air into and from the airbag and detecting the pressure.

Fifth, the cloth cover provided on the inner circumferential surface of the airbag must be large enough so that the airbag may be fully inflated and have a small inside diameter (The cloth cover is so large while the inside diameter is so small.). Therefore, the cloth cover has wrinkles or slackens before the compressed air is supplied into the airbag.

Sixth, the cloth cover, which frequently contacts the body parts of subjects and likely gets dirty, should be replaced by a clean one after some use. However, the cover cannot be easily removed from, or attached to, the housing of the sphygmomanometer.

The present invention has been made in view of the problems with the conventional cuff apparatus of body-part insertion type, particularly the cuff apparatus in which the cuff fits on the body part as compressed air is introduced into it. An object of the invention is to provide a cuff apparatus in which compressed air can be introduced into the cuff within a short time and which is easy to handle and assemble. Another object of the invention is to provide a sphygmomanometer which comprises such a cuff apparatus, which is easy to handle and assemble and which is small and lightweight.

BRIEF SUMMARY OF THE INVENTION

According to this invention, the objects described above can be attained by a cuff apparatus for measuring blood pressures, in which an airbag (a bladder) is provided in a chassis, in the form of a hollow cylinder, compressed air is introduced into the airbag to suppress a flow of blood in a body part. The cuff apparatus is characterized in that cushions are provided in the airbag so that the airbag remains in an inflated state before the compressed air is introduced into the airbag.

In a preferred embodiment of the invention, each of the cushions may have an uneven (wavy) side on a surface that opposes an inner circumferential surface of the airbag and may be fixed in the airbag and spaced apart from one another.

In another preferred embodiment of the present invention, a microphone is attached to a part of the inner circumferential surface of the airbag, at which a cushion is provided. Preferably, one of the cushions is fixed at almost a middle part of the airbag as developed, in a lengthwise direction of the airbag, two of the cushions are fixed and arranged symmetrically with respect to the one cushion in the lengthwise direction of the airbag, and microphones are provided in those parts of the inner circumferential surface of the airbag which oppose the two cushions arranged symmetrically.

In still another preferred embodiment of this invention, an elastic band-shaped member is secured to an outer circumferential surface of the airbag. Preferably, the band-shaped member is secured in the airbag so as to lie near an inlet port of the chassis while the airbag remains in the chassis and in the form of a hollow cylinder.

In a further preferred embodiment of the invention, the ends of the airbag as developed, which are spaced apart in the lengthwise direction of the airbag, overlap each other while the airbag remains in the chassis and in the form of a hollow cylinder. It is desired that an auxiliary cushion be provided within at least one of the ends of the airbag that overlap each other. Further, it is preferred that the auxiliary cushion should have a thickness gradually changing (increasing) in a direction perpendicular to a lengthwise of the airbag.

The present invention provides a cuff apparatus for measuring blood pressures, in which a plurality of fasteners are provided on an outer circumferential surface of an airbag, each having a flange shaped like a mushroom cap, and a chassis has engagement holes in which the flanges of the fasteners are fitted, thereby fastening the airbag to the chassis.

In a preferred embodiment of the invention, each of the engagement holes is shaped like a gourd, and is formed by a large hole and a small hole connected to each other, and each of the flanges shaped like a mushroom cap is moved from the large hole to the small hole to be set in the engagement hole.

In another preferred embodiment of this invention, each of at least one of the fasteners has a conduit for supplying and discharging compressed air into and from the airbag. Preferably, each of the fasteners has a conduit for detecting the pressure of compressed air in the airbag. Moreover, it is desired that cushions be provided in the airbag and maintain the airbag in an inflated state before compressed air is introduced into the airbag, and a filter be provided in the conduit for preventing chips of the cushions from entering the conduit.

In a further preferred embodiment of the invention, the inner circumferential surface of the hollow cylindrical airbag inserted in the chassis is covered with a cloth cover made of flexible fibers. Preferably, the cloth cover is formed in the shape of a hollow cylinder and has an elastic ring at each end, and elastic rings are fitted in recesses made in the housing of a sphygmomanometer so that the cloth cover may be removably secured to the housing.

Further, the present invention provides a sphygmomanometer that comprises a cuff apparatus of any type according to the invention.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIGS. 4A and 4B are perspective views, illustrating the chassis of the embodiment, seen from the inlet port and outlet port thereof, respectively;

DETAILED DESCRIPTION OF THE INVENTION

Figure 1:
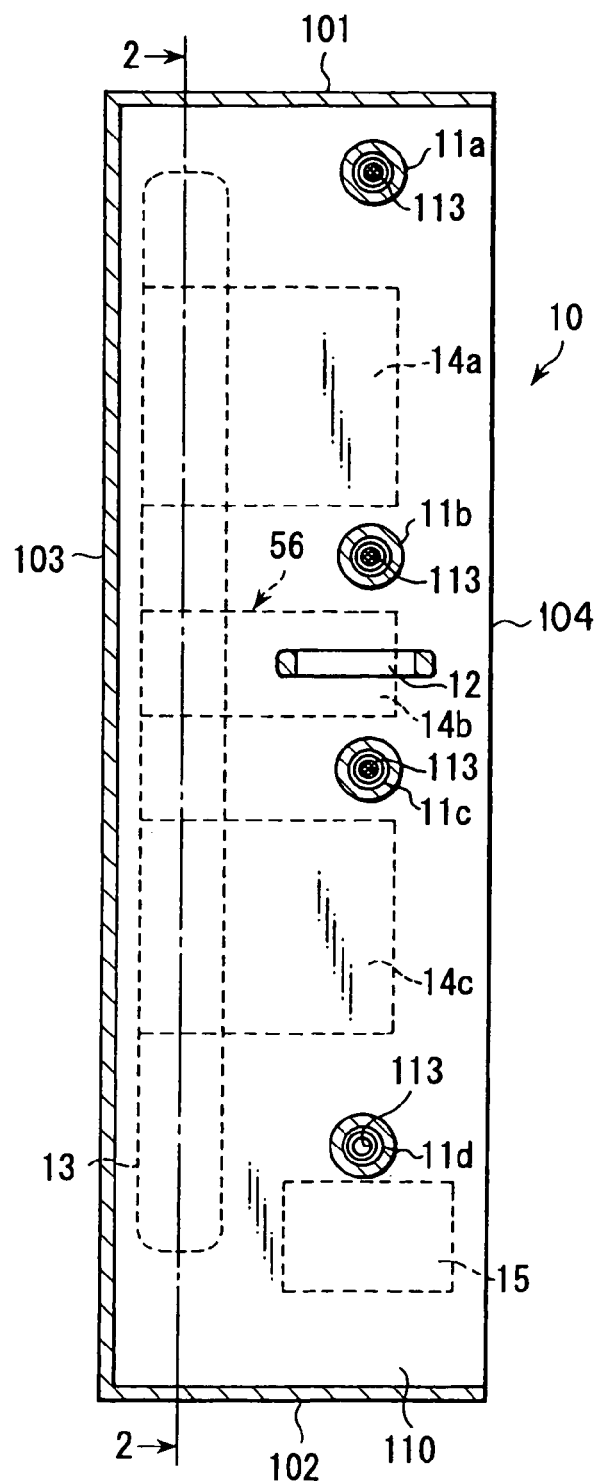
FIG. 1 is a side view of the airbag (the bladder) according to an embodiment of the invention, showing the outer circumferential surface of the developed airbag.

A cuff apparatus and a sphygmomanometer comprising a cuff apparatus, both according to the invention, will be described in detail, with reference to the preferred embodiments shown in the drawings attached hereto.

The cuff apparatus according to the embodiment is desired to measure the blood pressure in the upper arm (i.e., body part). It basically comprises an airbag (a bladder), a chassis (case) holding the airbag, and, preferably, a cloth cover for the airbag. The sphygmomanometer according to the embodiment is of the type that measures blood pressures by detecting the sound of the bloodstream (Korotkoff sound). Hence, the cuff apparatus has microphones for detecting the Korotkoff sound.

Figure 2:
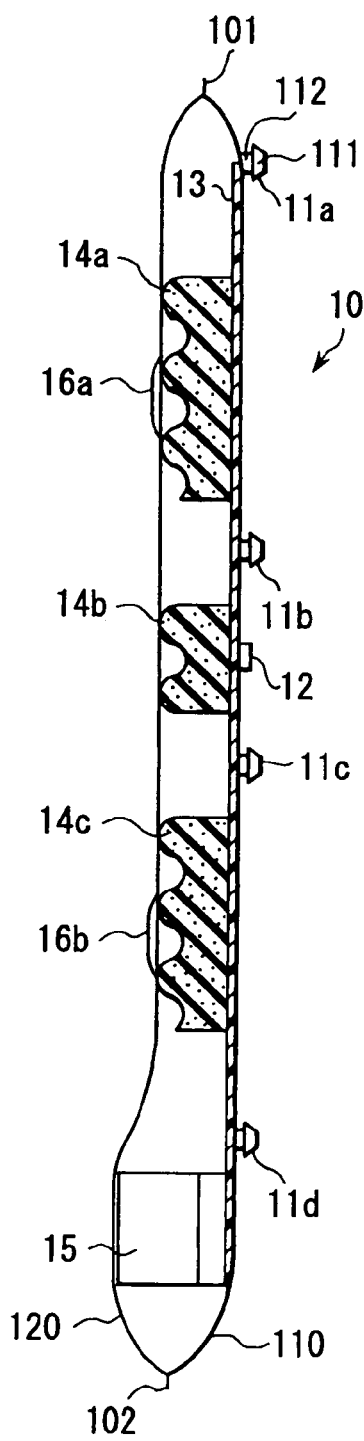
FIG. 2 is a cross-sectional view of the airbag, taken along line 2-2 shown in FIG. 1.
Figures 3A, 3B:
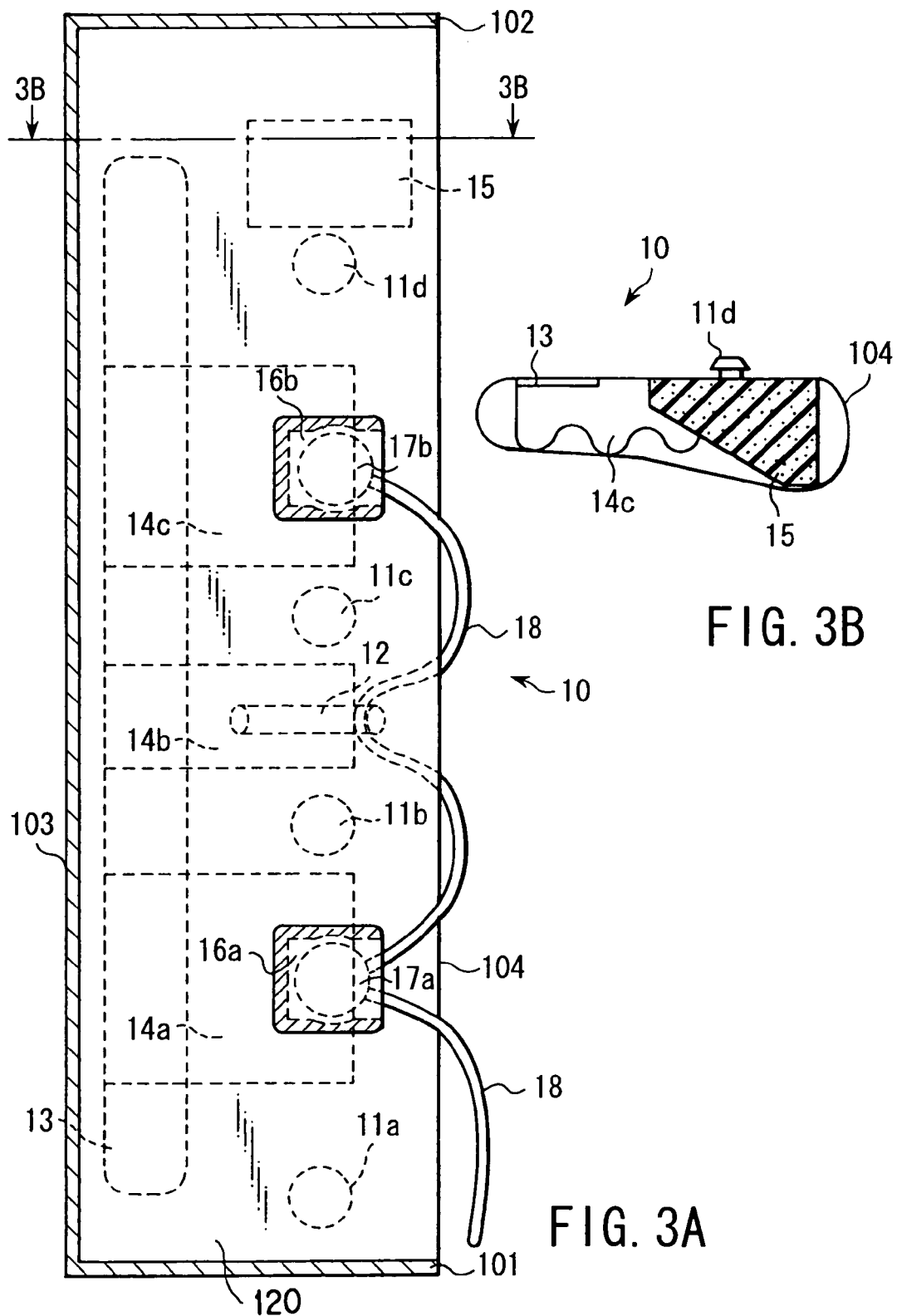
FIG. 3A is a side view of the airbag of the embodiment, depicting the inner circumferential surface of the developed airbag.
FIG. 3B is a cross-sectional view of the airbag, taken along line 3B-3B shown in FIG. 3A.

FIG. 1 shows the airbag developed, as viewed from the outer circumferential surface of the airbag (i.e., the surface remote from the body part while the airbag remains in the chassis and shaped like a hollow cylinder). FIG. 2 is a cross-sectional view of the airbag, taken along line 2-2 shown in FIG. 1. FIG. 3A depicts the airbag developed, as viewed from the inner circumferential surface of the developed airbag (i.e., the surface contacting the body part while the airbag remains in the chassis and shaped like a hollow cylinder). FIG. 3B is a cross-sectional view of the airbag, taken along line 3B-3B shown in FIG. 3A. As is illustrated in FIG. 3A, the microphones are attached to the airbag.

As FIG. 1 shows, the airbag 10 is substantially rectangular, when it is developed. It is about 13 to 14 cm wide (measured in a direction perpendicular to the lengthwise direction) and about 45 to 50 cm long (measured in the lengthwise direction). Both ends 101 and 102 (spaced apart in the lengthwise direction) and the one edge 103 (extending in the direction perpendicular to the lengthwise direction) are fused together by high-frequency welding, whereby a bag is formed. (The parts that are fused are shaded in FIG. 1.)

As seen from FIGS. 1 and 2, four fasteners 11a, 11b, 11c and 11d are secured to the outer circumferential surface 110 of the airbag 10 by means of high-frequency welding. (The parts high-frequency welded are shaded in FIG. 1.) The fasteners serve to attach the airbag 10 to the chassis (case). Each of the four fasteners 11 (numeral "11" is used generally for the reference marks 11a, 11b, 11c and 11d) comprises a flange 111 and a shank 112, as can been seen from the fastener 11a shown in FIG. 2. The flange 111 is shaped like a mushroom cap. As FIG. 1 depicts, each of the fasteners 11 have a hole 113. Each hole 113 of the fastener 11a, 11b, 11c functions as a duct (a conduit) that communicates with the interior of the airbag 10. Namely, each hole 113 of the fastener 11a, 11b, 11c is a through hole.

The four fasteners 11 are positioned a little closer to the edge 104 than to the opposite edge 103 fused by high-frequency welding, in the widthwise direction (i.e., the direction perpendicular to the lengthwise direction). In the lengthwise direction, the fasteners 11a and 11b are spaced apart by a distance, the fasteners 11c and 11d are spaced apart by the same distance, and the fasteners 11b and 11c are spaced apart by a shorter distance. The fasteners 11a and 11b are positioned not symmetrical to the fasteners 11c and 11d, with respect to the midpoint in the length of the airbag. The fasteners 11 are located, rather close to one end 101. When the airbag 10 is attached to the chassis that is a hollow cylinder, the part lying between the fasteners 11a and 11b and the part lying between the fasteners 11c and 11d are secured to the sides of the chassis. The part lying between the fasteners 11b and 11c is secured to the lower part of the chassis. The part lying between the fastener 11a and the neighboring end 101 (in the lengthwise direction) is secured to an upper part of the chassis. The part lying between the fastener 11d and the neighboring end 102 (in the lengthwise direction) is secured to the upper part of the chassis, too.

A cable holder 12 (a small rectangular sheet) is high-frequency welded, at its short sides, to the almost middle part of the outer circumferential surface 110 in the lengthwise direction of the airbag 10. (The parts high-frequency welded are shaded.)

As FIG. 2 shows, a band-shaped member 13 is bonded to the outer circumferential surface of the airbag 10, in the airbag 10, with double-side adhesive tape or the like. The member 13 is made of elastic substance such as polyethylene or polypropylene. It extends in the lengthwise direction of the airbag 10.

In the airbag 10, three cushions (main cushion members) 14a, 14b and 14c are secured, spaced apart from one another. The cushions are made of sponge-like material such as foamed urethane. An auxiliary cushion (auxiliary cushion member) 15 is secured in the airbag 10, near the end 102 of the airbag 10. The auxiliary cushion 15 is made of sponge-like material such as foamed urethane, too.

In FIG. 1 and FIG. 3A, the broken lines indicate the band-shaped member 13, the cushions 14 (numeral "14" is used generally for the reference marks 14a, 14b and 14c) and the auxiliary cushion 15, which are provided in the airbag 10 along with the fasteners 11 and the cable holder 12.

The band-shaped member 13 is located near the high-frequency welded edge 103 of the airbag 10, extends parallel to the edge 103 and is bonded to the airbag 10. The auxiliary cushion 15 is positioned closer to the edge 104 of the airbag 10 than to the opposite, high-frequency welded edge 103 and is secured to the airbag 10.

Of the three cushions 14a, 14b and 14c, one (i.e., the second cushion 14b) lies between the fasteners 11b and 11c. (The cushion 14b is located almost at the middle part of the airbag, or more precisely shifted a little toward the end 101, as seen from FIGS. 1, 2 and 3A.) The other cushions 14a and 14c lie symmetrically with respect to the second cushion 14b, spaced from the cushion 14b by about 40 mm in the lengthwise direction of the airbag 10. The auxiliary cushion 15 is provided between the fastener 11d and the end 102 (located near the fastener 11d) of the airbag 10.

The cushions 14 are secured to the surface opposed to the outer circumferential surface 110 of the airbag 10. They partly overlap the band-shaped member 13. That part of each cushion 14, which overlaps the band-shaped member 13, is fixed (secured) directly to the band-shaped member 13 with double-side adhesive tape or the like. That part of each cushion 14, which contacts the outer circumferential surface 110, is secured to (stuck on) the surface 110 with double-side adhesive tape or the like. The auxiliary cushion 15 is fixed (secured) to the outer circumferential surface 110 with double-side adhesive tape or the like.

The band-shaped member 13 is about 30 mm wide (measured in a direction perpendicular to the lengthwise direction of the airbag), about 400 mm long (measured in the lengthwise direction of the airbag), and about 1 to 2 mm thick.

Of the cushions 14, the cushion 14b located almost at the middle part of the airbag 10 is about 40 mm wide (measured in the lengthwise direction of the airbag), about 90 mm long (measured in a direction perpendicular to the lengthwise direction of the airbag), and about 25 mm thick at maximum. The cushions 14a and 14c, lying on the sides of the cushion 14b, are about 80 mm wide (measured in the lengthwise direction of the airbag), about 90 mm long (measured in a direction perpendicular to the lengthwise direction of the airbag), and about 25 mm thick at maximum.

The auxiliary cushion 15 is about 40 mm wide (measured in the lengthwise direction of the airbag) and about 60 mm long (measured in a direction perpendicular to the lengthwise direction of the airbag). The thickness of the auxiliary cushion 15 gradually increases (changes) from the minimum value of about 10 mm to the maximum value of about 40 mm, from the band-shaped member 13 toward the fasteners 11, as is illustrated in the cross-sectional view of FIG. 3B.

Each of the cushions 14 has an uneven (wavy) side that opposes the inner circumferential surface 120 of the airbag 10. In other words, each of cushions 14 has protrusions at this side. The protrusions have a length of, for example, about 10 mm.

As indicated above, the cushions 14 are provided in the airbag 10. That part of the airbag 10, which contains the cushions 14, is inflated to have a thickness of about 30 mm, even in its natural state or even before compressed air is supplied into the airbag 10. This reduces an amount of air that should be introduced into the airbag 10 to measure the blood pressure. Hence, the airbag 10 can be inflated to a desired extent within a shorter time.

The thickness that the airbag 10 has in its natural state is determined by the maximum thickness of the cushions 14. Even if the cushions 14 had no uneven (wavy) sides, they could inflate the airbag to the same extent as in this embodiment, provided that they are thick enough. In this case, too, the amount of air that should be introduced could indeed be decreased to shorten the time required for inflating the airbag. However, the uneven (wavy) sides reduce the force applied from the inner circumferential surface 120 of the airbag 10 to collapse the cushions 14, thereby to minimize the resistance to the upper arm (body part) being inserted into the cuff apparatus.

Unlike the cushions 14, the auxiliary cushion 15 has no wavy side opposing the inner circumferential surface 120 of the airbag 10. Nonetheless, its thickness gradually increases (changes) from the band-shaped member 13 toward the fasteners 11, in the widthwise direction of the airbag 10 (i.e., a direction perpendicular to the lengthwise direction). The auxiliary cushion 15 reduces the amount of the compressed air supplied into the airbag and, hence, shorten the time required to supply the compressed air, in the same way as the cushions 14 do. Additionally, as will be described later, the auxiliary cushion 15 holds the upper arm (body part) that contacts the inner circumferential surface 120 of the airbag 10, because it is located on the upper part of the chassis. Thus, it sets the airbag 10 in full contact with the upper-front part of the upper arm, preventing the upper arm from moving up or down while inserted in the cuff apparatus. This facilitates reliable measuring of the blood pressure.

The cushions 14 and the auxiliary cushion 15 are fixed (secured) in the airbag 10 and spaced apart from one another. Wrinkles, if any, will be formed at the parts of the airbag, at which the cushions are not provided. Virtually no wrinkles will be formed at those parts of the inner circumferential surface 120, where the cushions 14 and 15 are provided.

As seen from FIG. 3A, pockets 16a and 16b are attached to the inner circumferential surface 120 of the airbag 10, by means of high-frequency welding. (The welded parts of the pockets are shaded in FIG. 3A.) Each of the pockets 16a and 16b contains a microphone (17a or 17b), respectively. The microphones are connected by a cable 18. The cable 18 that connects the two microphones 17a and 17b passes through the cable holder 12 (indicated by broken lines in FIG. 3A) that is fixed to the sheet. The cable 18, which extends between the microphones 17a and 17b, is thereby secured to the airbag 10 by the cable holder 12. This makes it easy to attach the airbag 10 to the chassis.

The airbag 10 is shaped like a hollow cylinder. The airbag 10 is fastened to the inner surface of the chassis (case) that is a hollow cylindrical molding made of ABS resin or the like. More specifically, the airbag is secured to the chassis by setting the four fasteners 11a, 11b, 11c and 11d in four engagement holes 19a, 19b, 19c and 19d made in the chassis.

FIGS. 4A and 4B show the outer appearance of the chassis 20. FIG. 4A is a perspective view of the chassis 20, as seen from its inlet port, through which the arm (body part) is inserted into the airbag 10 inside the chassis 20. FIG. 4B is a perspective view of the chassis 20, as seen from its outlet port that is opposed to the inlet port. Each of the fasteners 11a, 11b, 11c and 11d, all provided on the airbag 10, is set in each of the engagement holes 19a, 19b, 19c and 19d, respectively.

A noise-sensor holder 21 is mounted on the upper part of the chassis 20. A noise sensor (not shown) is attached to the holder 21. The noise sensor thus secured to the chassis 20 may detect the noise that the microphones 17a and 17b have caught, not the sound of bloodstream. The noise may be one generated as the vibration of the table supporting the sphygmomanometer is transmitted to the housing of the sphygmomanometer. If the noise sensor detects such noise, it generates a noise signal. The noise signal detected by the microphones 17a and 17b is canceled by the noise signal detected by the noise sensor, whereby the sound of bloodstream flowing in the upper arm, i.e., the Korotkoff sound, can be reliably detected.

Two pump holders 22a and 22b and two solenoid valve holders 23a and 23b are provided on the lower part of the chassis 20. Each of the pump holders 22a and 22b holds a pump, whereas each of the solenoid valve holders 23a and 23b holds a solenoid valve. The pump supplies compressed air into the airbag 10. The solenoid valve discharges compressed air from the airbag 10.

Various projections 24 protrude from the outer circumferential surface of the cylindrical chassis 20 in the radial direction of the chassis 20. These projections 24 reinforce the chassis 20 and are used to position the chassis 20 when the chassis 20 is attached to the housing of the sphygmomanometer. When the chassis 20 is attached to the housing of the sphygmomanometer, dry cells (batteries) are set in a gap between the pump holder 22a and the solenoid valve holder 23a, on the one hand, and the pump holder 22b and the solenoid valve holders 23b, on the other hand. Alternatively stated, the dry cells (batteries) are accommodated right below the hollow cylindrical chassis 20, to supply electric power to drive the pump and the solenoid valve.

The engagement holes (openings) 19 (numeral "19" is used generally for reference marks 19a, 19b, 19c and 19d) are shaped like a gourd. As seen from the engagement holes 19c and 19b shown in FIGS. 4A and 4B, respectively, each engagement hole being formed by a large hole (opening) 191, a small hole (opening) 192 and a neck 193 connecting the holes 191 and 192. As seen from the engagement holes 19a and 19d, the peripheries of gourd-shaped engagement holes 19 are a little thicker than any other parts of the chassis 20.

The large hole 191 is larger than the flange 111 of each fastener 11, whereas the small hole 192 is smaller the flange 111. The neck 193 connecting the large hole 191 and small hole 192 is narrower than the shank 112 of the fastener 11. The airbag 10 is secured to the chassis 20 by setting the flange 111 of each fastener 11 in the associated engagement hole 19. More precisely, the flange 111 shaped like a mushroom cap is inserted into the chassis 20 through the large hole 191 and is slid into the small hole 192, while passing through the neck 193. The fasteners 11 are made of elastic material such as polyurethane resin. Therefore, the shank 112, which lies below the flange 111, can deform and pass through the neck 193 of the engagement hole 19.

Figure 5:
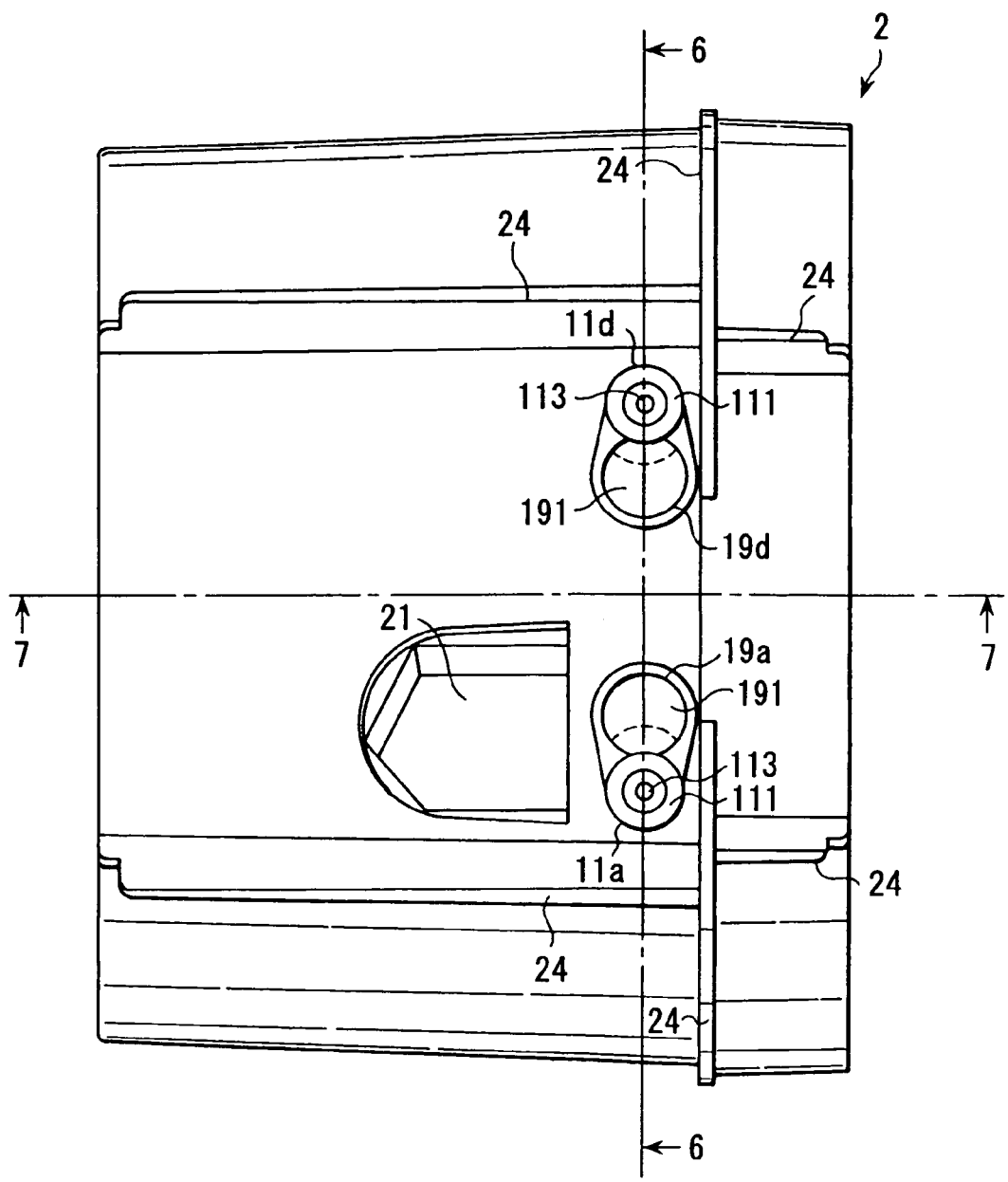
FIG. 5 is a plan view of the chassis of the embodiment, as seen from above, said chassis holding the airbag.
Figure 6:
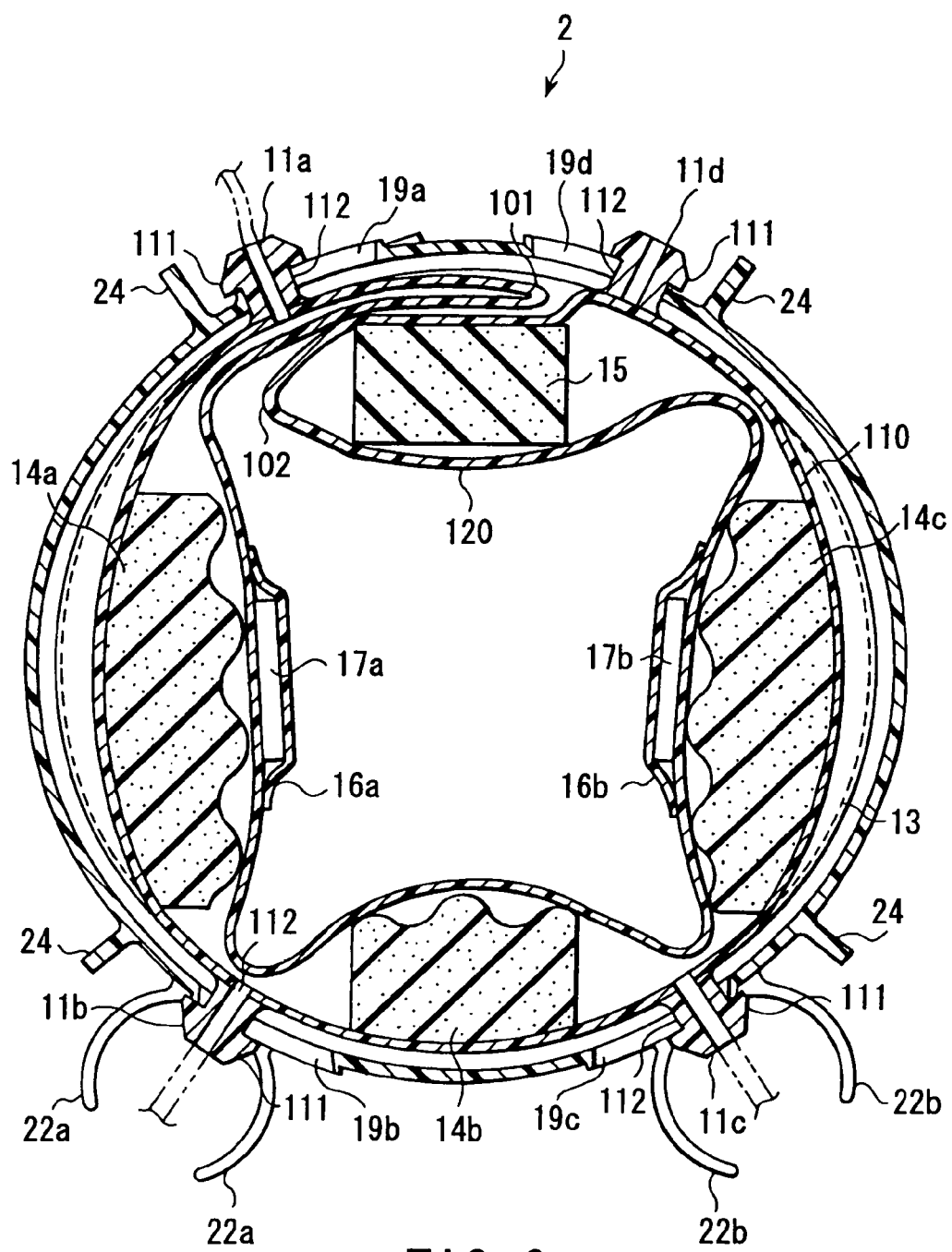
FIG. 6 is a cross-sectional view of the chassis holding the airbag, taken along line 6-6 shown in FIG. 5.
Figure 7:
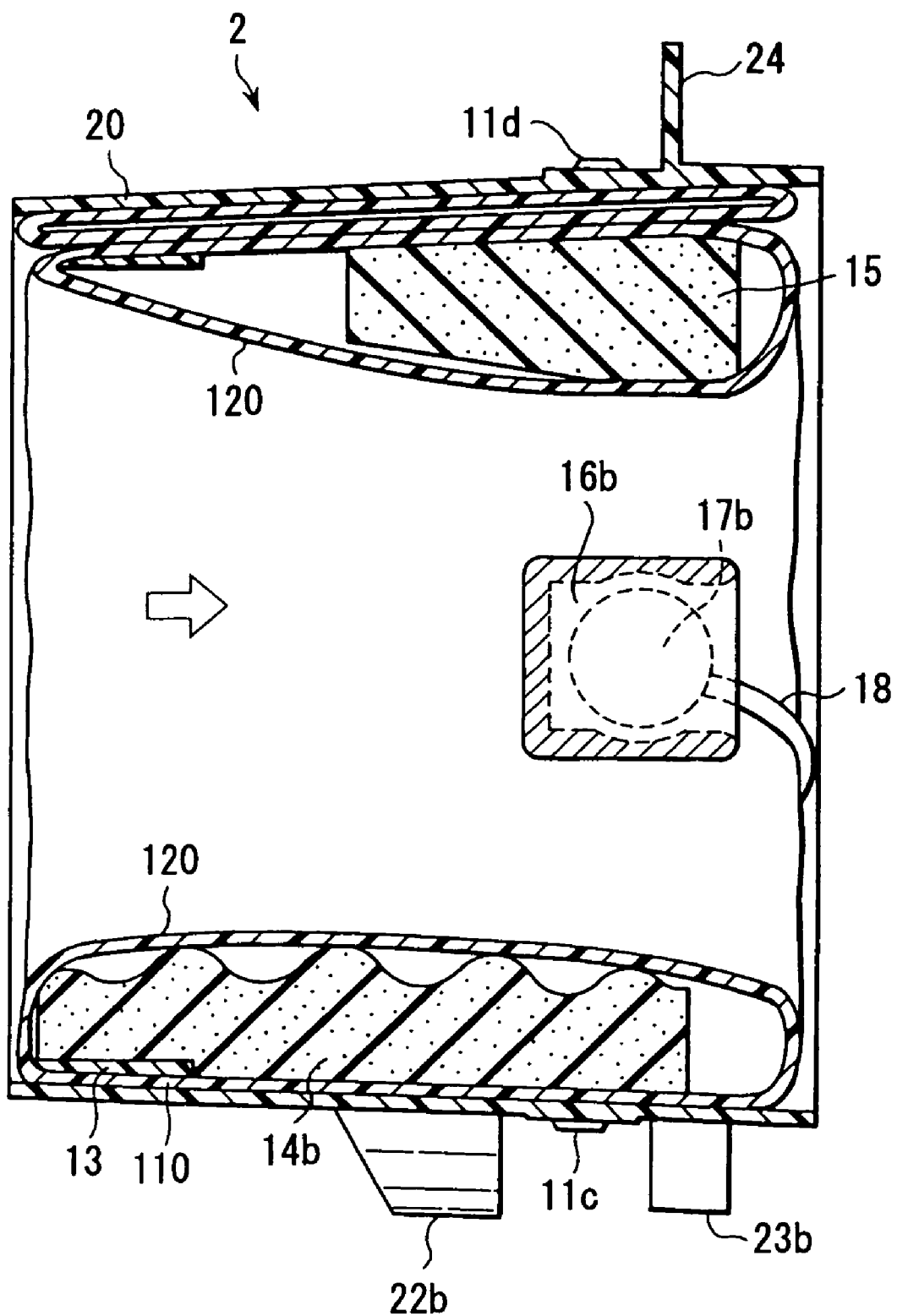
FIG. 7 is a cross-sectional view of the airbag, taken along line 7-7 shown in FIG. 5.

FIG. 5 is a plan view of the chassis 20 as seen from above, showing the airbag 10 attached to the chassis 20. FIG. 6 is a cross-sectional view of the chassis 20, taken along line 6-6 shown in FIG. 5, and FIG. 7 is a cross-sectional view of the chassis 20, taken along line 7-7 shown in FIG. 5. FIGS. 6 and 7 depict the interior of the chassis 20. FIGS. 5, 6 and 7 are also views that illustrate the basic structure of the cuff apparatus 2 according to the present embodiment.

FIG. 5 shows the flanges 111 of the fasteners 11a and 11d that have been moved from the large holes 191 to small holes 192 (not seen) of the engagement holes 19. Thus, the fasteners 11a and 11d are fitted in the engagement holes 19a and 19d, respectively.

The fastener 11a has a through hole 113 (conduit) that is connected to the interior of the airbag 10. The fastener 11a can function as a nozzle (conduit for compressed air). The pressure of the compressed air can therefore be detected through this conduit 113. Like the fastener 11a, each of the fasteners 11b and 11c has a through hole 113 (conduit) that is connected to the interior of the airbag 10. These conduits 113 connect the airbag 10 to the pumps and the solenoid valves, so that compressed air may be introduced into and discharged from the airbag 10. Thus, the fasteners 11b and 11c can function as nozzles (conduits for compressed air). The fastener 11d is identical in shape to the other fasteners 11a, 11b and 11c, it has a hole 113 but its hole 113 is not connected to the interior of the airbag 10. Namely, the hole 113 of the fastener 11d is not a through hole. Therefore, the fastener 11d cannot function as a nozzle.

The flanges 111 of the fasteners 11a, 11b and 11c, which are shaped like a mushroom cap, are moved into the small holes 192 of the engagement holes 19a, 19b and 19c, respectively. The fasteners 11a, 11b and 11c are thus set in the engagement holes 19a, 19b and 19c, respectively, so that the airbag 10 is attached to the chassis 20. Thereafter, connection pipes (shown in a broken line in FIG. 6) such as tubes, through which compressed air passes, are inserted into the through holes 113 of the fasteners. As the connection pipes are inserted into the holes 113, they apply a pressure, expanding the holes 113 in their radial direction. The shanks 112 located below the flanges 111 are therefore pressed onto the peripheries of the small holes 192 of the engagement holes 19. Hence, there is no risk that the fasteners 11a, 11b and 11c move back into the large holes 191 through the necks 193 of the engagement holes 19a, 19b and 19c and slip out of the engagement holes 19. Namely, the fasteners 11a, 11b and 11c remain fitted in the engagement holes 19 firmly and steadily.

Since each of the fasteners 11a, 11b and 11c can function as a nozzle (conduit for compressed air), no nozzle need to be used. If nozzles were used apart from fasteners, they must be held at desired positions in the chassis 20 while the airbag 10 is being secured to the chassis 20. Such an intricate work does not involve in assembling the cuff apparatus 2. The airbag 10 can be easily and firmly attached to the chassis 20, by using a simple fastening structure.

As indicated earlier, the airbag 10 incorporates cushions 14 and an auxiliary cushion 15. Chips may be formed from the cushions 14 and 15 as the cuff apparatus 2 is repeatedly used. The chips may enter the connection pipes connected to the pumps and the solenoid valves, through the holes 113 of the fasteners 11b and 11c, and may cause troubles in the pump and the solenoid valves. To prevent the chips from entering the connection pipes, mesh filters are provided in the holes 113 inside the shanks 112 of the fasteners 11b and 11c. In this embodiment, no filter is provided in the hole 113 of the fastener 11a, because the chips of the cushions are not so likely to pass through the hole 113 of the fastener 11a as through the holes 113 of the fasteners 11b and 11c which serve to supply and discharge compressed air. Nevertheless, a filter may be provided in the hole 113 of the fastener 11a, too, to prevent the chips of the cushions from entering the tube (i.e., connection pipe connected to a pressure sensor. If this is the case, the pressure can be measured more accurately.

The engagement holes 19b and 19c made in the lower part of the chassis 20 and the engagement holes 19d and 19a made in the upper part of the chassis 20 have a large hole 191 and a small hole 192, respectively. As FIG. 5 depicts, the small hole 192 is located more outwardly than the large hole 191. (That is, the small hole 192 is farther from the cross section of the chassis, taken along line 7-7, than the large hole 191.) This eliminates the possibility that the airbag 10 rotates in the chassis 20 and is dislocated.

The distance between the small holes 192 of the engagement holes 19b and 19c, both made in the lower part of the chassis 20, is equal to the distance between the fasteners 11b and 11c provided on the airbag 10. This achieves a stable attaching of the airbag 10 to the lower part of the chassis 20.

The ends 101 and 102 of the airbag 10, which are spaced apart in the lengthwise direction of the airbag 10, suppress the flow of blood but a little when they suppress independently. Nonetheless, they cooperate to effectively suppress the flow of blood since they overlap each other at the uppermost part of the chassis 20 as seen from FIG. 6. Therefore, the flow of blood can be reliably suppressed even if the body part is inserted in the cuff apparatus 2, with the arties positioned at the overlapping ends 101 and 102.

The cushions 14 and the auxiliary cushion 15 are fixed at different positions and spaced apart from each other in the airbag 10. Wrinkles are therefore formed at only those parts of the inner circumferential surface 120, where the cushions 14 and 15 are not fixed (i.e., the parts defining valleys shown in FIG. 6). Almost no wrinkles are formed at the parts of the inner circumferential surface 120, which oppose the cushions 14. The cushions 14a and 14c are fixed to those parts of the airbag 10 (or, inner sides of the chassis 20) which usually contact that part of the upper arm (body part) in which the arteries exist. The cushions 14a and 14c can serve to fully suppress the flow of blood in the arteries in either upper arm (body part). In addition, no wrinkles are formed at those parts of the inner circumferential surface 120. Since the microphones 17a and 17b are attached to those parts of the inner circumferential surface 120 which the cushions 14a and 14c oppose, the Korotkoff sound can be reliably detected no matter whether the left upper arm or the right upper arm is inserted in the cuff apparatus 2.

The pump holders 22a and 22b are provided on the lower part of the chassis 20 and position symmetrical to each other. The pumps held by the holders 22a and 22b are connected, together with the solenoid valves that lie near the pumps, to the fasteners 11b and 11c respectively that function as nozzles.

An arrow shown in FIG. 7 indicates a direction in which the arm is inserted into the cuff apparatus 2. The band-shaped member 13 is bonded to the outer circumferential surface 110 of the airbag 10 and in the vicinity of the inlet port of the chassis 20 through which the arm is inserted. Hence, the airbag 10 can be pushed, at its outer circumferential surface 110, onto the entire inner surface of the hollow cylindrical chassis 20. Thus, the airbag 10 secured to the chassis 20 would not be deformed or displaced when the arm is pulled from or inserted into the chassis 20. The airbag 10 is still more neither deformed nor displaced, as it is pressed against the chassis 20 at a position near the inlet port of the chassis 20.

The auxiliary cushion 15 is fixed to the inner circumferential surface of the airbag 10 and positioned near the outlet port of the chassis 20, with its thickness gradually increasing toward the outlet port of the chassis 20. Therefore, when the upper arm (body part) is inserted into the cuff apparatus, the fore slender portion of the upper arm (i.e., the portion near the forearm) fits well. This prevents the upper arm from moving in the vertical direction. In addition, this maintains the microphones for detecting the Korotkoff sound, in such a stable condition that they oppose a specific portion of the upper arm.

Figure 8:
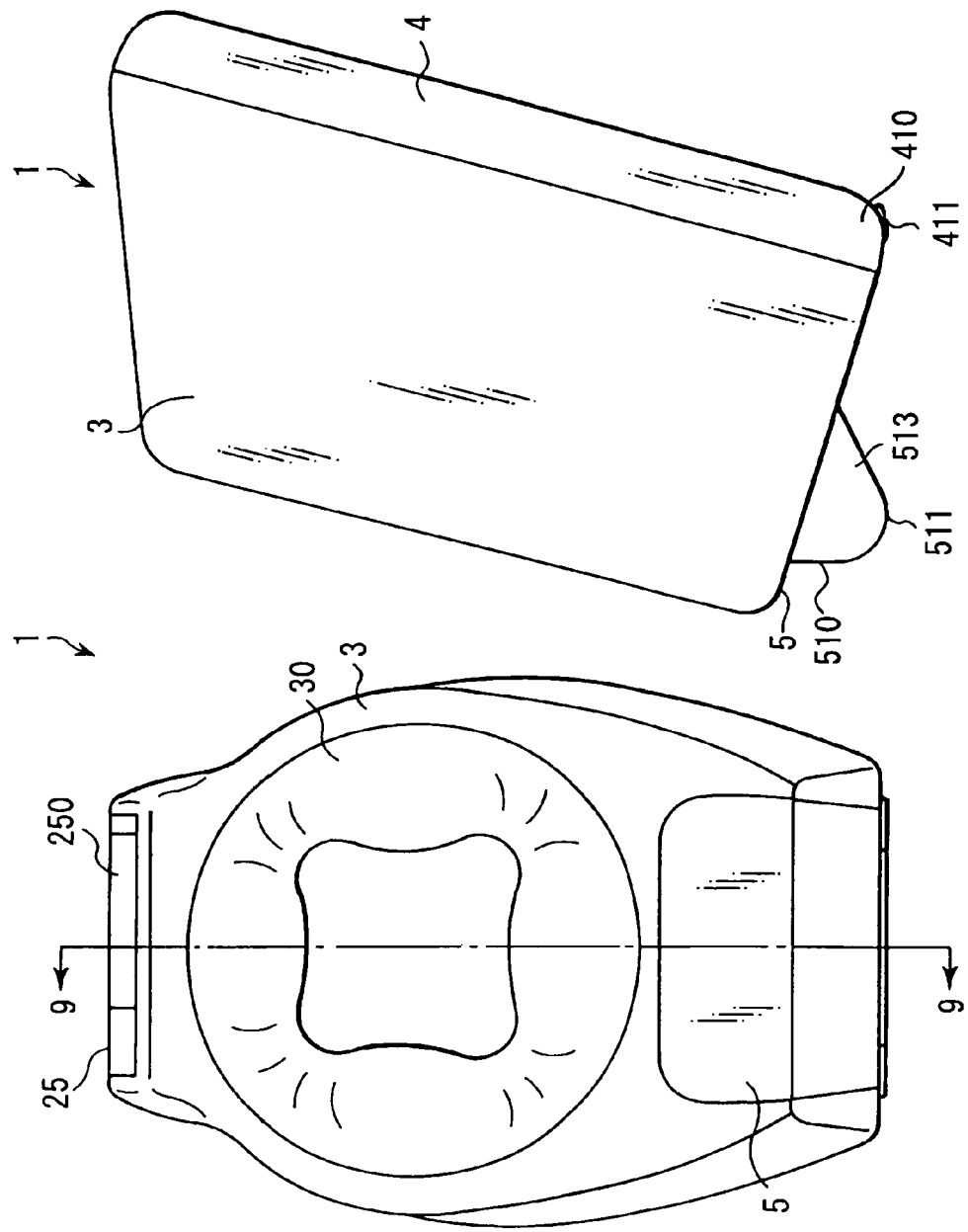
FIGS. 8A and 8B are a font view and side view, respectively, of a sphygmomanometer according to an embodiment of the invention.
Figure 9:
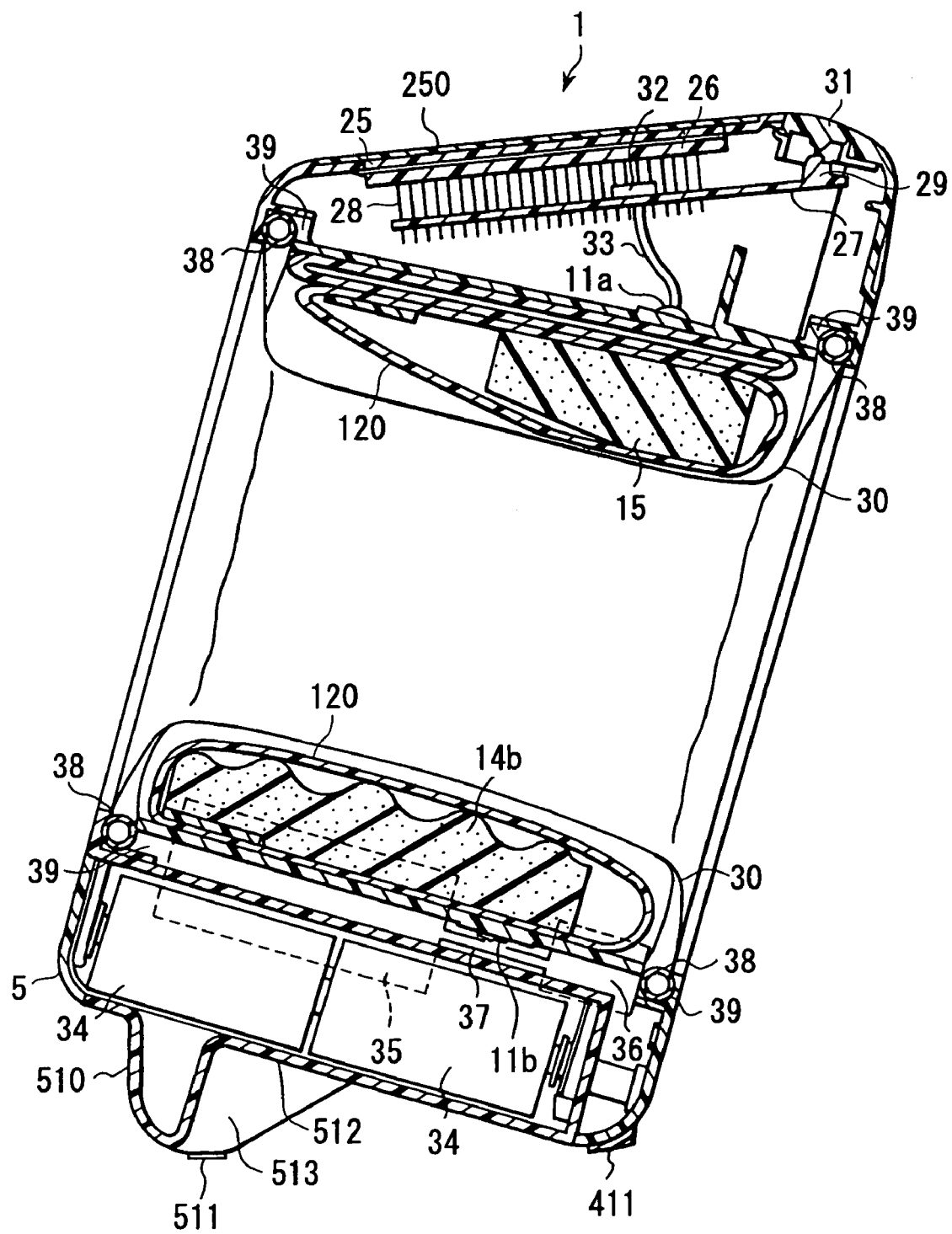
FIG. 9 is a vertical sectional view of the sphygmomanometer, taken along line 9-9 shown in FIG. 8A.

FIGS. 8A and 8B are a font view and side view, respectively, of a sphygmomanometer 1 that comprises the cuff apparatus 2 according to the present embodiment. In FIG. 8B, the front of the sphygmomanometer 1 is shown in the left-hand part. FIG. 9 is a vertical sectional view of the sphygmomanometer 1, taken along line 9-9 shown in FIG. 8A.

As seen from FIG. 8B, the housing of the sphygmomanometer 1 comprises a casing 3, a casing cover 4, and a battery cover 5. The casing 3 defines the front of the sphygmomanometer 1. The casing cover 4 defines the back of the sphygmomanometer 1 (i.e., the side opposed to the front). The battery cover 5 define the bottom of the sphygmomanometer 1. The sphygmomanometer 1 further comprises a circuit board. The circuit board is offered in the casing 3, together with the cuff apparatus 2, the pumps, the solenoid valves, and the like. Then, the casing cover 4 closes the casing 3. The battery cover 5 is fastened to the lower part of the casing 3 after the dry cells are installed. Through the above procedure the components are held in place within the housing. A projection (leg) 510 extends downwards from the front of the battery cover 5. The leg 510 causes the sphygmomanometer 1 to incline at such an angle that the arm may be smoothly inserted into the cuff apparatus 2.

The leg 510 has slip-preventing members 511 at its ends 513. The members 511 are made of urethane rubber and contact a table as long as the sphygmomanometer 1 is put on the table. A slip-preventing member 411, made of urethane rubber, too, is bonded to almost the entire lower part of the casing cover 4, which has a rounded surface 410 (i.e., the part of the cover 4, which extends from the left to the right in FIG. 8A).

A display panel 25 with a protection film attached to it is mounted in an upper part of the sphygmomanometer 1. The panel 25 comprises a liquid crystal display section 250 for displaying the blood pressure measured and the pulse rate measured. Further, a measuring start switch and a measuring stop switch (not shown in FIG. 8A or FIG. 8B) are provided on the upper part of the sphygmomanometer 1, at the back of the display panel 25 (i.e., the side opposed to the front of the panel 25).

As FIG. 9 shows, a liquid crystal plate 26, a substrate 27, and a plurality of pins 28 are provided with the liquid crystal display section 250, which forms a part of the display panel 25, in the upper part of the sphygmomanometer 1. The pins 28 extend from the liquid crystal plate 26 to the substrate 27. An internal switch 29 is provided on the substrate 27. The switch 29 operates in interlock with a measuring start or stop switch 31 that is mounted on the outer surface of the sphygmomanometer 1. A pressure sensor 32 is provided on the substrate 27 and connected to the through hole (conduit) of the fastener 11a that is provided on the airbag 10. The sensor 32 can therefore detect the pressure of the compressed air applied into the airbag 10.

Four dry cells (batteries) 34 are provided in the lowermost part of the sphygmomanometer 1. The cells 34 are arranged in two rows spaced apart in the widthwise direction of the sphygmomanometer 1 (i.e., the horizontal direction in FIG. 8A), each row consisting of two cells. The pump 35 for supplying compressed air and the solenoid valve 36 for discharge compressed air, which are indicated by broken lines, are accommodated on the upper and outer side of the dry cells 34 in the sphygmomanometer 1. A tube 37 connects both the pump 35 and the solenoid valve 36 to the through hole of the fastener 11b provided on the airbag 10.

The leg 510 has a bottom plate 512 that supports the dry cells at its center part. Therefore, the center part of the leg 510 (i.e., a part near the cross section taken along line 9-9) is thicker (narrower) than the end parts spaced apart in the widthwise direction (i.e., the horizontal direction in FIG. 8A).

As seen from FIGS. 8A and 9, the cuff apparatus according to this embodiment has a cloth cover 30. The cover 30 covers the inner circumferential surface 120 of the airbag 10.

The cloth cover 30 is shaped like a hollow cylinder. Elastic rings 38, such as nylon tubes, are mounted on the ends of the cloth cover 30. The rings 38 are fitted in the recesses 39 formed in the housing of the sphygmomanometer 1, whereby the cloth cover 30 is secured to the housing, covering the inner circumferential surface 120 of the airbag 10.

Figure 10A:
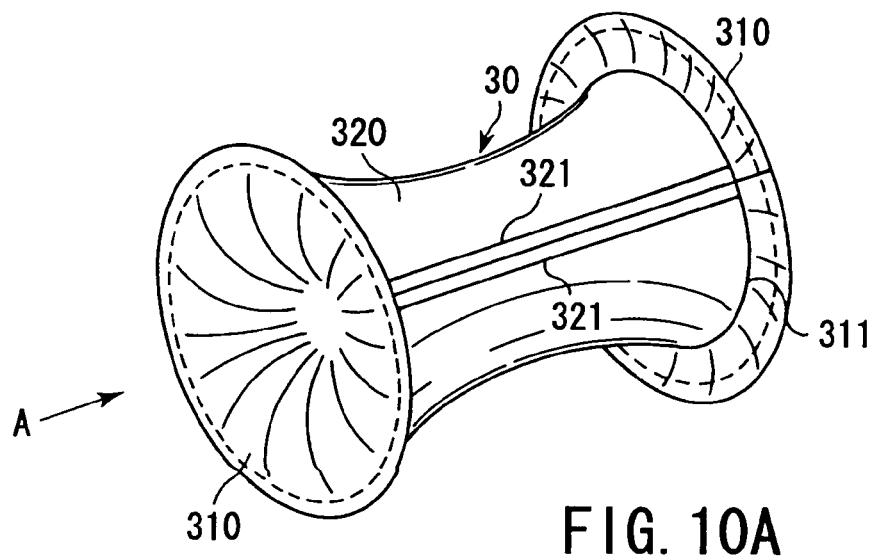
FIGS. 10A, 10B and 10C are a perspective view, a front view and a side view, respectively, of the cloth cover of a cuff apparatus according to an embodiment of the invention.
Figure 10B:
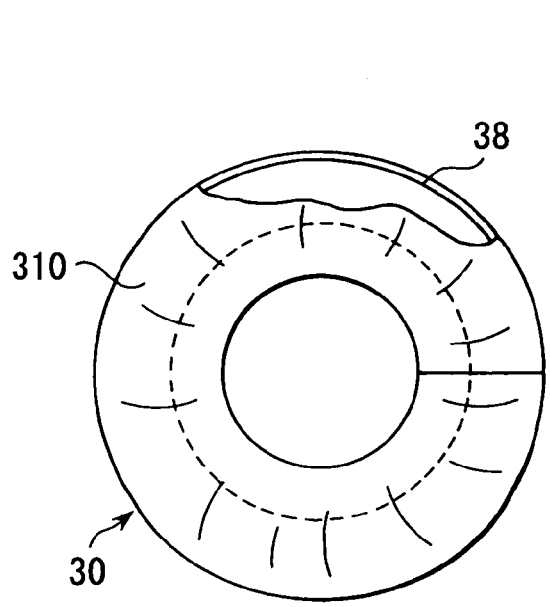
Figure 10C:
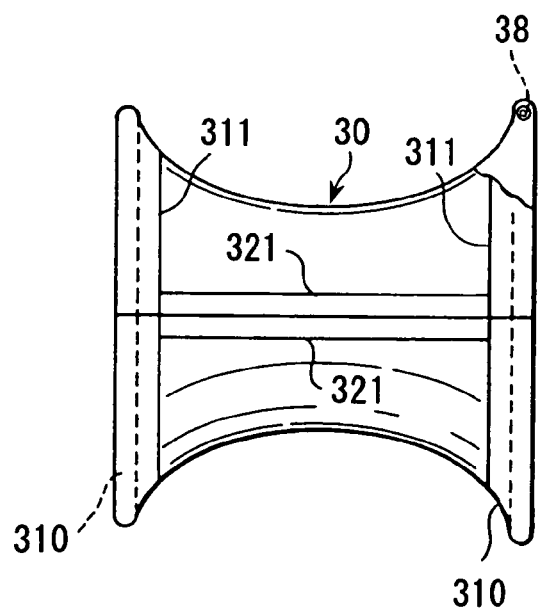

FIGS. 10A is a perspective view of the cloth cover 30 secured to the housing of the sphygmomanometer 1. The cover 30 is made by rolling a sheet of cloth into a hollow cylinder. Both ends of the cover 30 are sewed, wrapping the elastic rings 38. Once secured to the housing, the cloth cover 30 assumes the shape of an hourglass. FIG. 10B shows one end of the cover 30 as viewed in the direction of arrow A shown in FIG. 10A (or, as viewed from said one end), said one end containing the elastic ring 38. FIG. 10B is cross-sectional in part, showing a part of the elastic ring 38 contained in the end of the cover 30. FIG. 10C depicts the cover 30 as viewed from a direction at right angles to arrow A shown in FIG. 10A, illustrating the seam on the cover 30. FIG. 10C is a partly cross-sectional, too, showing a cross section of a part of one end that contains the elastic ring 38. In FIG. 10C, the broken lines indicate the seams and the solid lines 311 and 321 indicate the edges of the cloth.

The cloth cover 30 is made of flexible fibers, like bi-directionally stretchable fibers such as nylon fibers in the main (80% nylon fibers and 20% polyurethane fibers). Therefore, the cover 30 covering the inner circumferential surface 120 of the airbag 10 can freely expand and contract in both the lengthwise direction of the airbag 10 and the widthwise direction thereof (i.e., direction perpendicular to the lengthwise direction). Namely, the cover 30 can readily expand and contract in accordance with the diameter of the upper arm (body part) inserted into the airbag 10 and exerting a pressure on the airbag 10. Thus, the cover 30 expands as the airbag 10 is inflated to hold the body part having the smallest diameter possible, even if the cloth cover 30 has a diameter corresponding to the largest diameter possible of the body part so as not to slacken. The cloth cover 30 would not therefore be torn. The cloth cover 30 may have a diameter corresponding to the smallest diameter possible of the body part so as not to slacken. In this case, too, as the body part that has the largest diameter possible is inserted in the airbag 10, the cover 30 can expand well and would not be torn.

Figure 11:
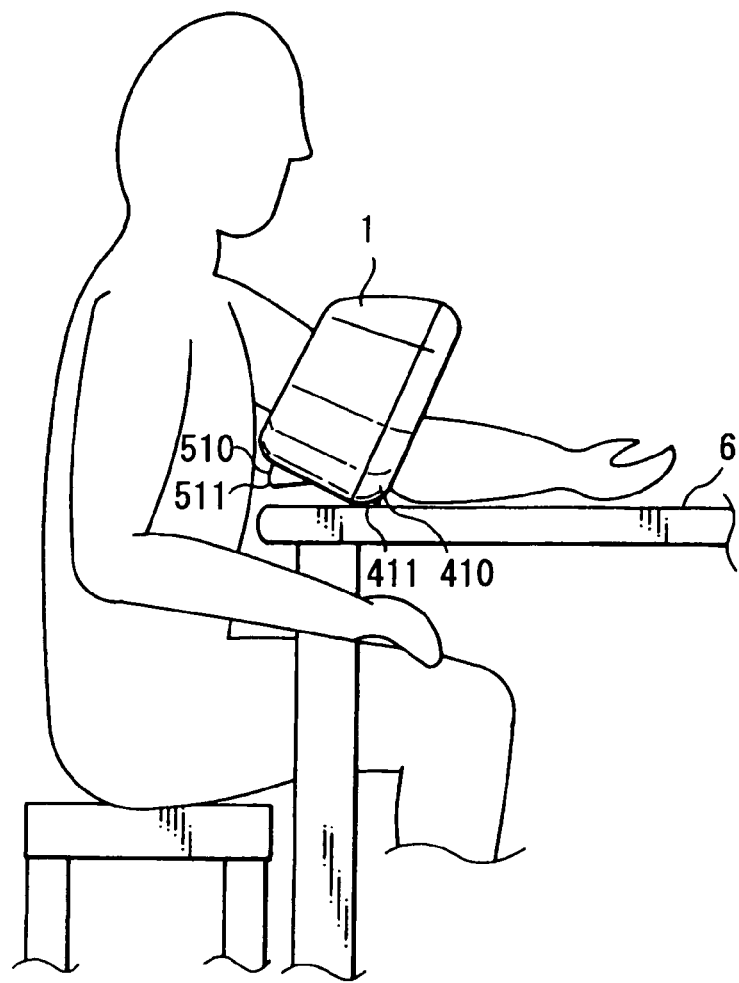
FIG. 11 is a pictorial view, showing a subject undergoing the blood-pressure measuring by the use of the sphygmomanometer according to the embodiment.
Figure 12:
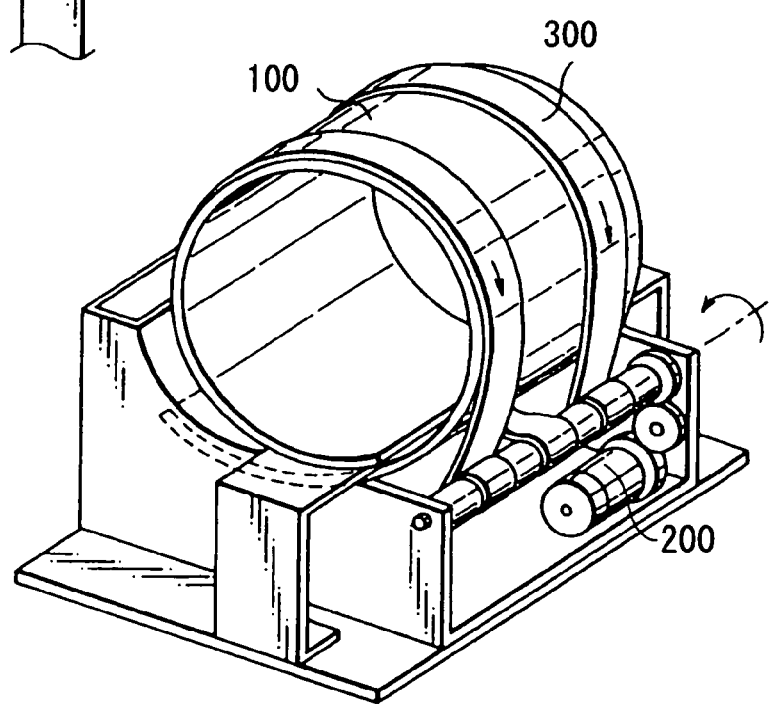
FIG. 12 is a perspective view of a conventional cuff apparatus in which the cuff is taken up.

FIG. 11 shows a subject undergoing the blood-pressure measuring by the use of the sphygmomanometer 1 according to the invention, with his or her upper arm (body part) inserted in the cuff apparatus 2. The housing of the sphygmomanometer 1 has a rounded bottom 410 (the bottom of the casing cover 4) at the rear part. The slip-preventing member 411 made of urethane rubber is bonded to almost the entire lower part of the casing cover 4. Similarly, the slip-preventing member 511 made of polyurethane, too, is bonded to each end 513 of the bottom at the front (the projection 510 of the battery cover 5). The members 411 and 511 prevent the sphygmomanometer 1 from slipping on the table 6 on which the sphygmomanometer 1 is placed. This facilitates reliable measuring of the blood pressure in the upper arm of the subject.

In any sphygmomanometer with a cuff apparatus into which the upper arm (body part) is inserted to measure the blood pressure, the body part (upper arm) should lie parallel to the axis of the arm-holding, hollow cylindrical section of the cuff apparatus, in order to suppress the flow of blood in the upper arm as is desired. When the sphygmomanometer 1 according to this embodiment is used, the body part (upper arm) can set in parallel to the axis of the arm-holding, hollow cylindrical section of the cuff apparatus 2. This is because the housing of the sphygmomanometer 1 inclines around the rounded bottom of the cuff apparatus 2 (the bottom having the slip-preventing member 411 bonded to and functioning as a fulcrum) corresponding to the angle at which the body part (upper arm) is inserted to the hollow cylindrical section (i.e., the chassis). The sphygmomanometer 1 can therefore reliably suppress the flow of blood and accurately measure the blood pressure, while the subject sits in a comfortable position, not in an unnatural position.

The cuff apparatus and the sphygmomanometer 1 having the cuff apparatus, both according to this invention, have been described with reference to preferred embodiments shown in the accompanying drawings. Nonetheless, the present invention is not limited to the embodiments explained above. For instance, the body part of which the blood pressure is measured may be the wrist or the forearm, instead of the upper arm as in the embodiment described above.

As has been explained, the cuff apparatus of this invention, designed for use in measuring blood pressures, has an airbag in which cushions are provided and held inflated before compression air is introduced into them. Thus, the cushions help to shorten the time required to supply the compressed air into the airbag. Further, each cushion has a uneven (wavy) part on its inner circumferential surface (the surfaces opposing the body part). This minimizes the resistance to the body part being inserted into the cuff apparatus. This makes it possible for the body part to enter the cuff apparatus smoothly.

Further, since the cushions are fixed in the airbag and spaced apart from one another, wrinkles, if any, will be formed at the parts of the airbag, which lie between the cushions. Virtually no wrinkles will be formed at those parts of the inner circumferential surface, where the cushions are provided. Thus, the ability of suppressing the flow of blood scarcely decreases. Namely, the cushions provided at those parts of the airbag, which lie near the arteries existing in the body part, serve to minimize the error of measuring the blood pressure.

In the cuff apparatus for use in sphygmomanometers that measure blood pressures by detecting the Korotkoff sound, a microphone is attached to a part of the inner circumferential surface of the airbag, at which a cushion is provided. The microphone can therefore contact closely the body part after compressed air has been introduced into the airbag. The microphone can reliably detect the Korotkoff sound. This can realize high-accuracy measuring of the blood pressure.

Moreover, one cushion is fixed in the airbag and located at almost the middle part of the airbag as developed, in the lengthwise direction thereof. And two cushions are fixed and positioned symmetrically with respect to said one cushion. The microphones are attached to the cushions symmetrically positioned. Thus, the microphones are set at such positions as reliably detect the Korotkoff sound from the both body parts (the right arm and the left arm) after the compressed air has been introduced into the airbag. This ensures high-precision measuring of the blood pressure in the both body parts.

In addition, a band-shaped member having elasticity is bonded to the outer circumferential surface of the airbag. This member prevents the airbag from being deformed or displaced when the body part is inserted into and pulled from the cuff apparatus. In particular, as the band-shaped member is provided in the airbag at a position near the inlet port of the chassis, it sufficiently prevents the airbag from being deformed when the arm is pulled from or inserted into the cuff apparatus.

Further, the ends of the airbag, which are spaced apart in the lengthwise direction of the airbag, overlap each other after the airbag shaped like a hollow cylinder has been inserted into the chassis. Hence, the flow of blood can be reliably suppressed even if the body part is inserted in the cuff apparatus, with the arteries positioned at the overlapping ends.

Furthermore, the auxiliary cushion secured in at least one end of the airbag, which overlaps the other end thereof, helps to shorten the time required to supply the compressed air into the airbag. In addition, the auxiliary cushion makes the body part contact, at its upper part, the airbag when the body part is inserted into the cuff apparatus, and therefore prevents the body part from moving in the vertical direction. This also ensures reliable measuring of the blood pressure in the body part. Particularly, the auxiliary cushion, whose thickness gradually changes (increases) in a direction perpendicular to the lengthwise of the airbag, fits well on the body part, thus preventing the body part from moving up or down. This maintains the microphone(s) in such a stable condition that they oppose a specific portion of the body part to detect the Korotkoff sound, in the cuff apparatus of the sphygmomanometer that measures blood pressures by detecting the Korotkoff sound.

Moreover, a plurality of fasteners are provided in the outer circumferential surface of the airbag, each having a flange shaped like a mushroom cap, and the chassis has engagement holes in which the flanges may be set. This enable the airbag to be secured to the chassis easily. Each engagement hole is shaped like a gourd, and is formed by a small hole, a large hole and a neck. As the flange of each fastener is moved from the large hole into the small hole, the airbag is fastened to the chassis easily and reliably.

Still further, each of the fasteners has a conduit. The conduit made in the fastener serves to supply compressed air into and discharge the same from the airbag or to detect the pressure of the compressed air. No nozzles need to be provided for supplying compressed air, discharging the same or detecting the pressure of the same. Additionally, there is no need to maintain such nozzles at desired positions in the process of attaching the airbag to the chassis. The airbag can thus be secured to the chassis easily and firmly by the use of a simple structure.

Moreover, filters are provided in the conduits made in the fasteners. The filters prevent the chips of the cushions from entering the connection pipes that are connected to the pumps, the solenoid valves and the pressure sensor. This prevents the chips to cause troubles in the pumps, the solenoid valves and the pressure sensor. Compressed air can be applied into and discharged from the airbag in a desired manner, and the pressure can be measured accurately.

The inner circumferential surface of the hollow cylindrical airbag inserted in the chassis is covered with a cloth cover made of flexible fibers. The cloth cover can expand in accordance with the size of the body part inserted or the degree of inflation of the airbag. Thus, the cloth cover will have no wrinkles or will not slacken.

Further, the cloth cover formed in the shape of a hollow cylinder has an elastic ring at each end. The elastic rings are fitted in the recesses formed in the housing of the sphygmomanometer, whereby the cloth cover is removably secured to the housing.

The sphygmomanometer according to the invention, which comprises the cuff apparatus that has the above-mentioned advantages, is easy to assemble and operate and is small and light.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cuff apparatus for measuring blood pressure in left and right upper arms, comprising:
   a chassis;
   a hollow cylindrical airbag having inner and outer walls, and received in the chassis, for suppressing a flow of blood of a human body by the inner wall when compressed air is introduced into the airbag;
   a plurality of cushions provided in the airbag, for causing the airbag to remain in an inflated state before compressed air is introduced into the airbag;
   said plurality of cushions comprising first, second and third cushions, and an auxiliary cushion, the first, second, third and auxiliary cushions each possessing a width as measured in a circumferential direction of the cylindrical airbag and a length measured in a direction of a longitudinal axis of the cylindrical airbag;
   the first, second, third and auxiliary cushions being arranged in that order in the airbag considered with reference to the circumferential direction of the airbag;
   the width of both the first cushion and the width of the third cushion being greater than the width of both the second cushion and the width of the auxiliary cushion;
   the auxiliary cushion possessing a thickness that increase in the length-wise direction of the auxiliary cushion; and
   first and second microphones which are arranged in the airbag to oppose each other, so that the first microphone detects Korotkoff sounds at the right upper arm of the human body near arties thereof when the right upper arm is inserted through and covered with the hollow cylindrical airbag and the compressed air is introduced into the airbag, and the second microphone detects Korotkoff sounds at the left upper arm of the human body near arties thereof when the left upper arm is inserted through and covered with the hollow cylindrical airbag and the compressed air is introduced into the airbag.

2. A cuff apparatus according to claim 1, wherein each of the first, second and third cushions has one side surface attached to an inside of the outer wall of the airbag, and has an opposite side surface that is wavy-shaped.

3. A cuff apparatus according to claim 1, wherein the cushions are fixed on an inside of the outer wall of the airbag, and spaced apart from one another in a circumferential direction.

4. A cuff apparatus according to claim 1, wherein said first and second microphones are attached to portions of an outside of the inner wall at circumferential positions on the airbag corresponding to circumferential positions of the first and third cushions.

5. A cuff apparatus according to claim 1, wherein the first and third cushions are arranged symmetrically with respect to the second cushion in a circumferential direction of the cylindrical airbag;
said first and second microphones are attached to portions of an outside of the inner wall at circumferential positions on the airbag corresponding to circumferential positions of the first and third cushions.

6. A cuff apparatus according to claim 1, which further comprises an elastic band-shaped member attached to an inner side of the outer wall.

7. A cuff apparatus according to claim 6, wherein the elastic band-shaped member is arranged on an inlet side of the airbag through which the upper arm is inserted into the airbag, and extended in a circumferential direction of the cylindrical airbag.

8. A cuff apparatus according to claim 1, wherein the cylindrical airbag is formed by bending an elongated rectangular airbag strip in a cylindrical shape, and overlapping opposite end portions of the airbag strip in a longitudinal direction thereof.

9. A cuff apparatus according to claim 8, wherein the auxiliary cushion is attached to an inner side of the outer wall near the overlapping opposite end portions of the airbag strip.

10. A cuff apparatus according to claim 9, wherein the thickness of the auxiliary cushion gradually increases in an insert direction of the upper arm.

11. A cuff apparatus according to claim 1, which further comprises a pair of pockets attached to an inner side of the inner wall of the airbag, each of the microphones being positioned in each one of the pockets.

12. A cuff apparatus according to claim 11, which further comprises a cable holder attached to the airbag between the pockets, and a cable connecting the microphones and supported by the cable holder.

13. A cuff apparatus according to claim 1, in which a plurality of fasteners are fixed to the airbag and extend outwardly away from an outer circumferential surface of the airbag, each having a flange shaped like a mushroom cap, and the chassis has engagement holes in which the flanges of the fasteners are fitted, thereby fastening the airbag to the chassis.

14. A cuff apparatus according to claim 13, wherein each of the engagement holes is shaped like a gourd, and is formed by a relatively large through hole and a relatively small through hole connected to each other, and each of the flanges shaped like a mushroom cap is inserted into the relatively large through hole and is moved from the relatively large through hole to the relatively small through hole to be set in the engagement hole.

15. A cuff apparatus according to claim 13, wherein each of the fasteners has a through conduit therein for supplying and discharging compressed air into and from the airbag.

16. A cuff apparatus according to claim 13, wherein each of the fasteners has a conduit therein for detecting pressure of the compressed air in the airbag.

17. A cuff apparatus according to claim 15, wherein a filter is provided in the conduit for preventing chips of the cushions from entering the conduit.

18. A cuff apparatus according to claim 1, wherein an inner circumferential surface of the hollow cylindrical airbag received in the chassis is covered with a cloth cover made of flexible fibers.

19. A cuff apparatus according to claim 18, wherein the cloth cover is formed in the shape of a hollow cylinder and has an elastic ring at each end, and the elastic rings are fitted in recesses formed in a housing of a sphygmomanometer, whereby the cloth cover is removably secured to the housing.

20. A cuff apparatus for measuring blood pressure in left and right upper arms of a human body, comprising:
a cylindrical chassis having an inner surface;
a hollow cylindrical airbag having inner and outer walls and an upper arm receiving space encircled by the inner wall for alternatively receiving the left upper arm and the right upper arm, the airbag being secured to the chassis so that the outer wall of the airbag faces the inner surface of the chassis, the airbag suppressing flow of blood of the upper arm of the human body by the inner wall when compressed air is introduced into the airbag;
a plurality of spaced apart cushions in the airbag which cause the airbag to be in an inflated state before compressed air is introduced into the airbag;
said plurality of cushions comprising first, second and third cushions, and an auxiliary cushion, the first, second, third and auxiliary cushions each possessing a width as measured in a circumferential direction of the cylindrical airbag and a length measured in a direction of a longitudinal axis of the cylindrical airbag;
the first, second, third and auxiliary cushions being arranged in that order in the airbag considered with reference to the circumferential direction of the airbag;
the width of both the first cushion and the width of the third cushion being greater than the width of both the second cushion and the width of the auxiliary cushion;
the auxiliary cushion possessing a thickness that increase in the length-wise direction of the auxiliary cushion; and
first and second microphones positioned in facing relation to one another at diametrically opposite positions across the upper arm receiving space so that the first microphone detects Korotkoff sounds at the right upper arm of the human body near arties thereof when the right upper arm is inserted through and covered with the hollow cylindrical airbag and the compressed air is introduced into the airbag, and the second microphone detects Korotkoff sounds at the left upper arm of the human body near arties thereof when the left upper arm is inserted through and covered with the hollow cylindrical airbag and the compressed air is introduced into the airbag.

21. A cuff apparatus according to claim 20, wherein the first, second and third cushions are fixed on an inner side of the outer wall, the first and third cushions being arranged symmetrically with respect to the second cushion in a circumferential direction of the cylindrical airbag, said first and second microphones being attached to portions of an outside of the inner wall at positions corresponding to the first and third cushions.

22. A cuff apparatus according to claim 21, wherein the airbag possesses an inlet side at one axial end of the cylindrical airbag through which the upper arm is inserted into the airbag and an outlet side at the opposite axial end of the airbag, and wherein the auxiliary cushion is attached to an inner side of the outer wall, the auxiliary cushion possessing an intermediate portion between opposite axial ends of the auxiliary cushion whose thickness gradually increases in a direction toward the outlet side of the airbag.

23. A cuff apparatus according to claim 22, wherein the first, second and third cushions each possess a wavy-shaped side opposing an inner circumferential surface of the airbag, the auxiliary cushion possessing a side opposing the inner circumferential surface of the airbag that is not wavy-shaped.

24. A cuff apparatus according to claim 20, wherein the airbag possesses an inlet side at one axial end of the cylindrical airbag through which the upper arm is inserted into the airbag and an outlet side at the opposite axial end of the airbag, and further comprising a circumferentially extending elastic band-shaped member attached to an inner side of the outer wall of the airbag, the elastic band-shaped member being positioned closer to the inlet side of the airbag than the outlet side of the airbag.

25. A cuff apparatus according to claim 20, further comprising a pair of pockets attached to an inner side of the inner wall of the airbag, each of the microphones being positioned in one of the pockets, a cable holder attached to the airbag at a position between the pockets, and a cable connecting the microphones and supported by the cable holder.

26. A cuff apparatus according to claim 20, wherein the airbag is secured to the chassis by a plurality of fasteners provided on an outer circumferential surface of the airbag, each of the fasteners being positioned in a respective engagement hole provided in the chassis, at least one of the fasteners positioned in the engagement hole in the chassis to secure the airbag to the chassis possessing a through hole that communicates with an interior of the airbag to supply compressed air to the interior of the airbag and discharge compressed air from the interior of the airbag.

27. A cuff apparatus according to claim 1, wherein the width of the first cushion and the third cushion is about 80 mm, the length of the first cushion and the third cushion is about 90 mm, the first cushion and the third cushion posses a maximum thickness of about 25 mm, the width of the second cushion is about 40 mm, the length of the second cushion is about 90 mm, the maximum thickness of the second cushion is about 25 mm, the width of the auxiliary cushion is about 40 mm, the length of the auxiliary cushion is about 60 mm, and the thickness of the auxiliary cushion changes from a minimum thickness of about 10 mm to a maximum thickness of about 40 mm.

28. A cuff apparatus according to claim 20, wherein the width of the first cushion and the third cushion is about 80 mm, the length of the first cushion and the third cushion is about 90 mm, the first cushion and the third cushion posses a maximum thickness of about 25 mm, the width of the second cushion is about 40 mm, the length of the second cushion is about 90 mm, the maximum thickness of the second cushion is about 25 mm, the width of the auxiliary cushion is about 40 mm, the length of the auxiliary cushion is about 60 mm, and the thickness of the auxiliary cushion changes from a minimum thickness of about 10 mm to a maximum thickness of about 40 mm.

* * * * *